United States Patent
Siochi

(10) Patent No.: US 6,577,707 B2
(45) Date of Patent: Jun. 10, 2003

(54) EDGE EXTENSION OF INTENSITY MAP FOR RADIATION THERAPY WITH A MODULATING MULTI-LEAF COLLIMATOR

(75) Inventor: Ramon Alfredo Carvalho Siochi, Apex, NC (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 39 days.

(21) Appl. No.: 10/021,118

(22) Filed: Oct. 30, 2001

(65) Prior Publication Data

US 2003/0081721 A1 May 1, 2003

(51) Int. Cl.⁷ .............................................. A61N 5/10
(52) U.S. Cl. ............................................ 378/65; 378/147
(58) Field of Search .......................... 378/65, 147, 145, 378/158, 64, 151, 152, 159, 153

(56) References Cited

U.S. PATENT DOCUMENTS

| | | | |
|---|---|---|---|
| 5,663,999 A | | 9/1997 | Siochi .......................... 378/65 |
| 5,724,403 A | | 3/1998 | Siochi et al. ................ 378/150 |
| 6,108,400 A | * | 8/2000 | Siochi .......................... 378/65 |
| 6,134,296 A | * | 10/2000 | Siochi .......................... 378/65 |
| 6,240,161 B1 | * | 5/2001 | Siochi .......................... 378/65 |
| 6,314,159 B1 | * | 11/2001 | Siochi .......................... 378/65 |
| 6,330,300 B1 | * | 12/2001 | Siochi .......................... 378/65 |
| 6,349,129 B1 | * | 2/2002 | Siochi .......................... 378/65 |

* cited by examiner

*Primary Examiner*—Drew A. Dunn
*Assistant Examiner*—Irakli Kiknadze

(57) ABSTRACT

A method for defining an extended field area of an intensity map for use in delivering radiation from a radiation source to an object with a multi-leaf collimator is disclosed. The multi-leaf collimator includes a plurality of leaves operable to travel in a first direction and rotatable such that the leaves are operable to travel in a second direction extending generally orthogonal to the first direction. The method includes defining a central square area having dimensions approximately equal to two times an over travel margin of the multi-leaf collimator and defining four edge margins each extending from a side of the central square and having dimensions approximately equal to two times an over travel margin of the multi-leaf collimator along an edge adjacent to the central square and half the number of leaves within the multi-leaf collimator times leaf width minus half the central square dimension. The central square and four edge margins define a field area for an intensity map deliverable with the multi-leaf collimator positioned such that leaves travel in the first and second directions.

20 Claims, 7 Drawing Sheets

EDGE EXTENSION OF INTENSITY MAP FOR RADIATION THERAPY WITH A MODULATING MULTI-LEAF COLLIMATOR

FIELD OF THE INVENTION

The present invention relates generally to radiation therapy, and more particularly, to a method and system for extending the field area of an intensity map used in radiation therapy with a modulating multi-leaf collimator.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

Conventional treatment planning systems are designed to only allow for radiation delivery with intensity maps having dimensions generally equal to the number of leaves*leaf width in the direction perpendicular to leaf motion and equal to the (leaf over travel*2)+(pencil beam width*2) in the leaf travel direction. These field sizes are the results of mechanical limitations at a collimator setting for arbitrary intensity distributions. Thus, conventional systems are limited to a fixed field size, collimator setting, and arbitrary intensity distributions.

There is, therefore, a need for a system and method that allows for field sizes that are beyond the field sizes imposed by mechanical constraints of a multi-leaf collimator.

SUMMARY OF THE INVENTION

A method for defining an extended field area of an intensity map for use in delivering radiation from a radiation source to an object with a multi-leaf collimator is disclosed. The multi-leaf collimator includes a plurality of leaves operable to travel in a first direction and is rotatable such that the leaves are operable to travel in a second direction extending generally orthogonal to the first direction. The method generally comprises defining a central square area having dimensions approximately equal to two times an over travel margin of the multi-leaf collimator and defining four edge margins each extending from a side of the central square and having dimensions approximately equal to two times an over travel margin of the multi-leaf collimator along an edge adjacent to the central square, and half the number of leaves within the multi-leaf collimator times leaf width minus half the central square dimension. The central square and four edge margins define a field area for an intensity map deliverable with the multi-leaf collimator positioned such that leaves travel in the first and second directions.

A system for defining an intensity map for use in delivering radiation from a radiation source to an object using a multi-leaf collimator generally comprises a processor operable to define a central square area having dimensions approximately equal to two times an over travel margin of the multi-leaf collimator and define four edge margins each extending from a side of the central square and having dimensions approximately equal to two times an over travel margin of the multi-leaf collimator along an edge adjacent to the central square, and half the number of leaves within the multi-leaf collimator times leaf width minus half the central square dimension. The central square and four edge margins define a field area for an intensity map deliverable with the multi-leaf collimator positioned such that leaves travel in the first and second directions. The system further includes memory configured to at least temporarily store the intensity map.

A method for delivering radiation from a radiation source to an extended field area with a multi-leaf collimator generally comprises creating an intensity map having boundaries defined by two rectangles each having dimensions approximately equal to two times an over travel margin of the multi-leaf collimator and the number of leaves of the multi-leaf collimator times leaf width. The two rectangles are arranged such that the center of the rectangles have the same central axis and are positioned orthogonal to one another.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
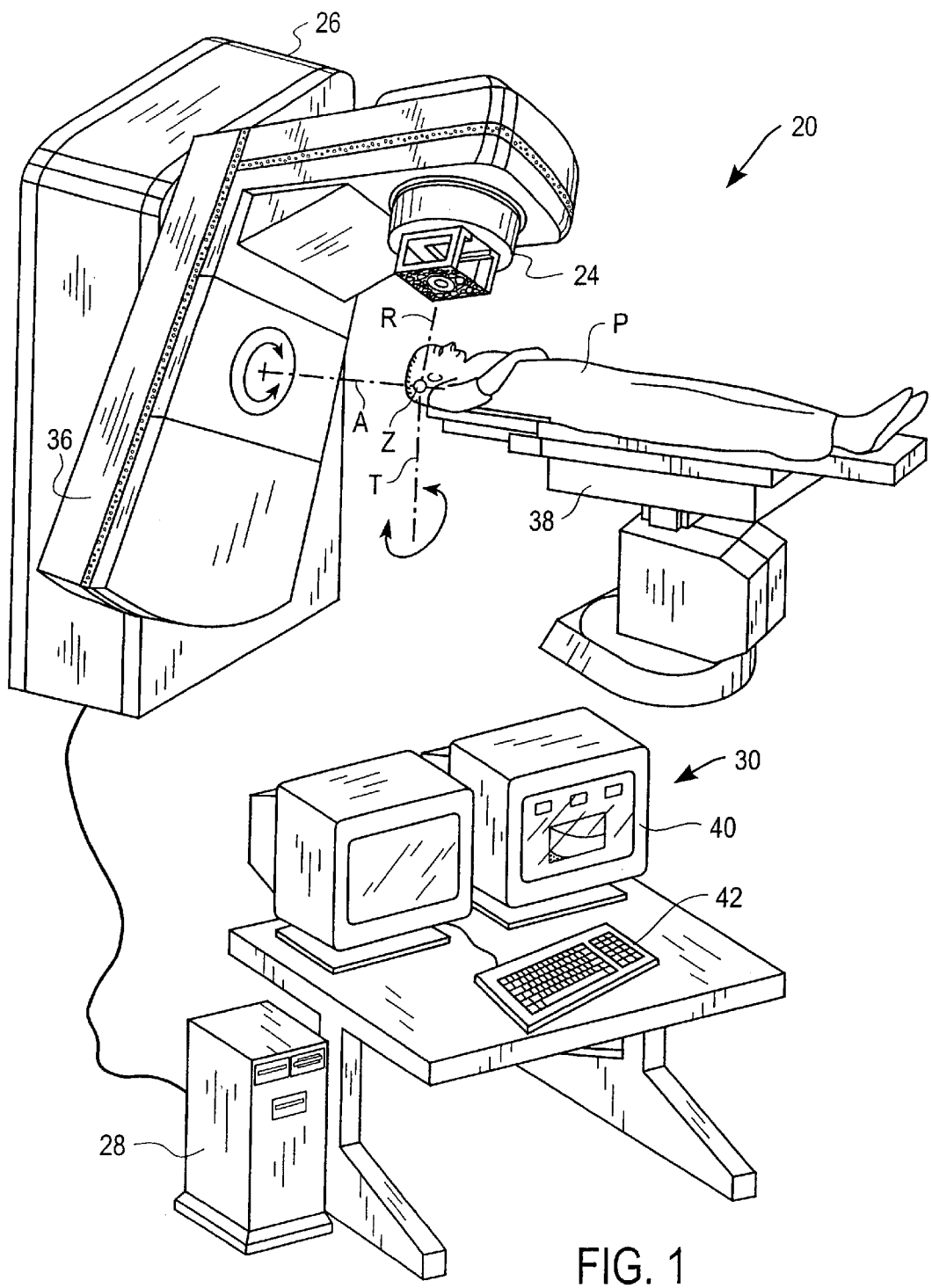
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
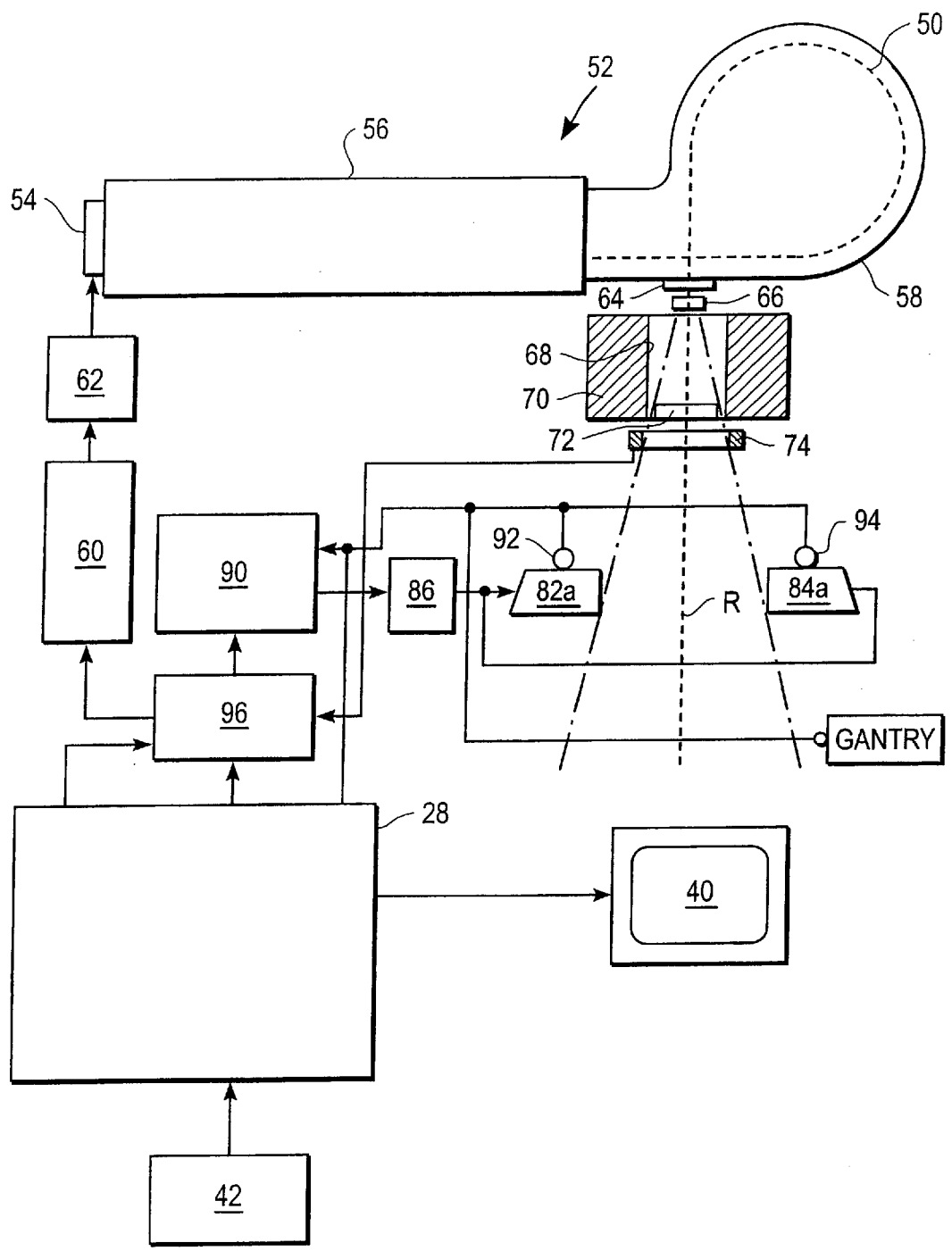
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
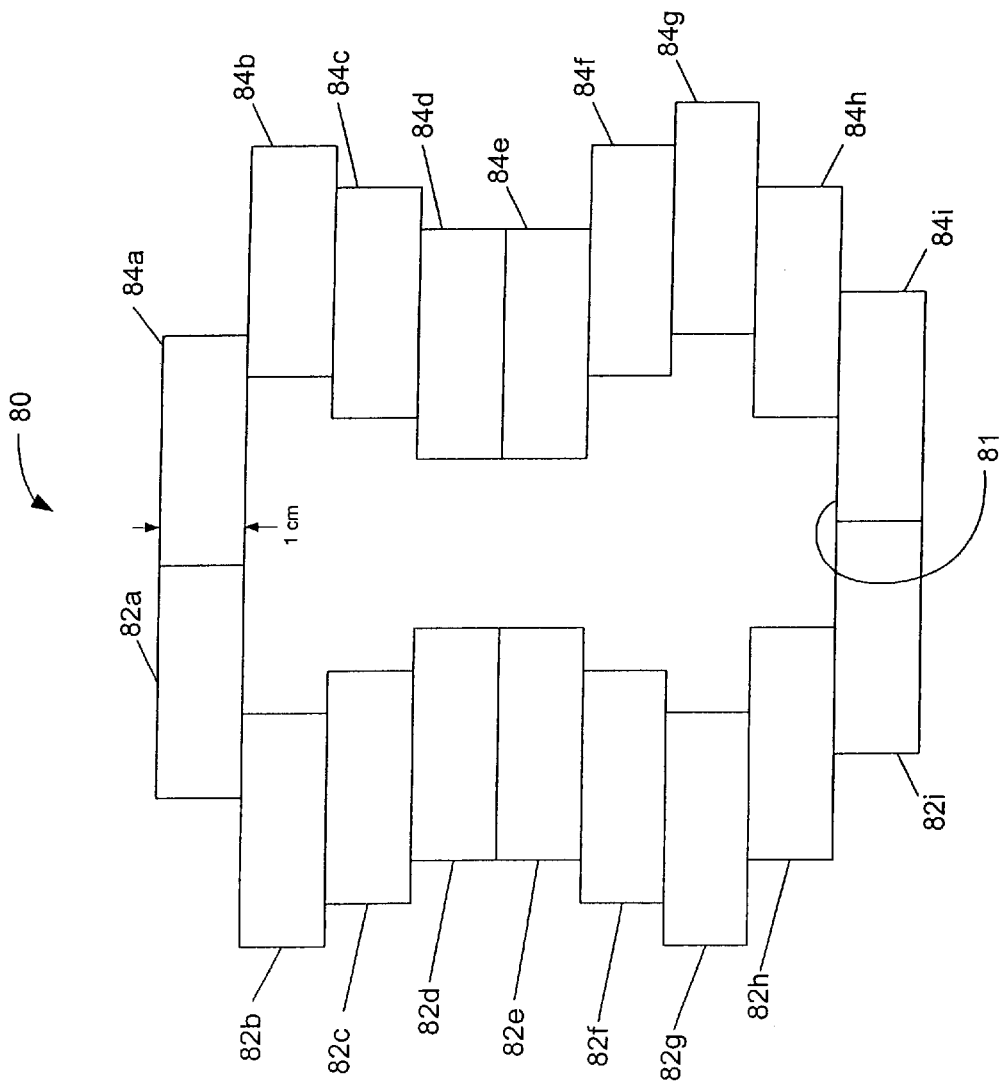
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82–i, 84a–i typically have a one centimeter width and are substantially impervious to the emitted radiation so that they block healthy tissue from the radiation.

The leaves 82–i, 84a–i are movable in a direction generally perpendicular to axis R by a drive unit 86 (which is shown in FIG. 2 only with respect to plate 82) to change the size of the irradiated field so that the distribution of radiation over the field does not need to be uniform (i.e., one region may be exposed to a higher dose than another region). The drive unit 86 includes an electric motor which is coupled to the plate 82 and controlled by a motor controller 90. Position sensors 92, 94 are also coupled to plates 82, 84*a*, respectively, for sensing their positions. The drive unit 86 drives the plate 82 in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82, 84*a*. The central processing unit 28 controls execution of the program and the opening and closing of the collimator plates 82, 84*a* to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the process described below.

Figure 4:
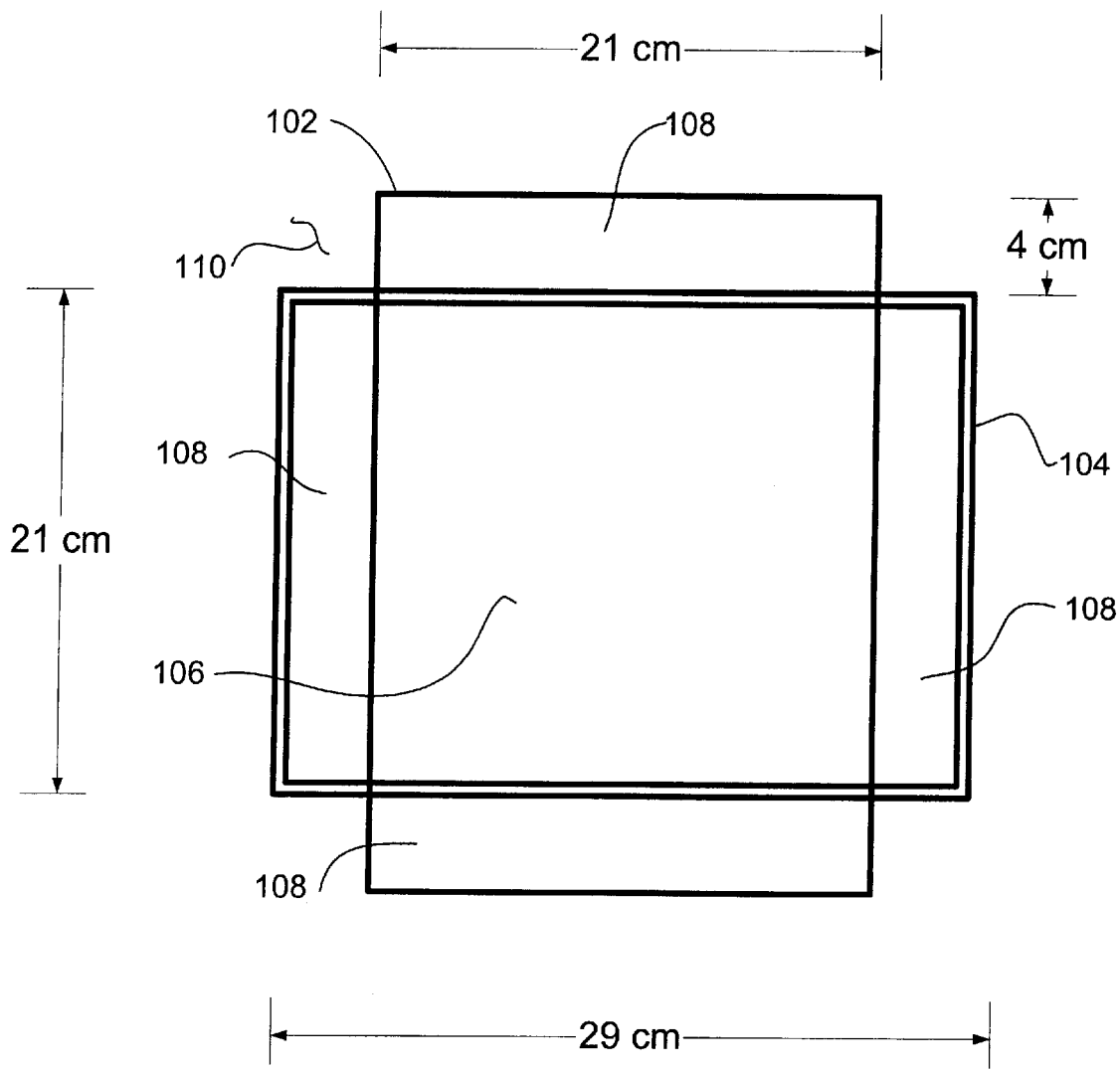
FIG. 4 is a schematic illustrating an intensity map field expanded by orthogonal decomposition.
Figure 5:
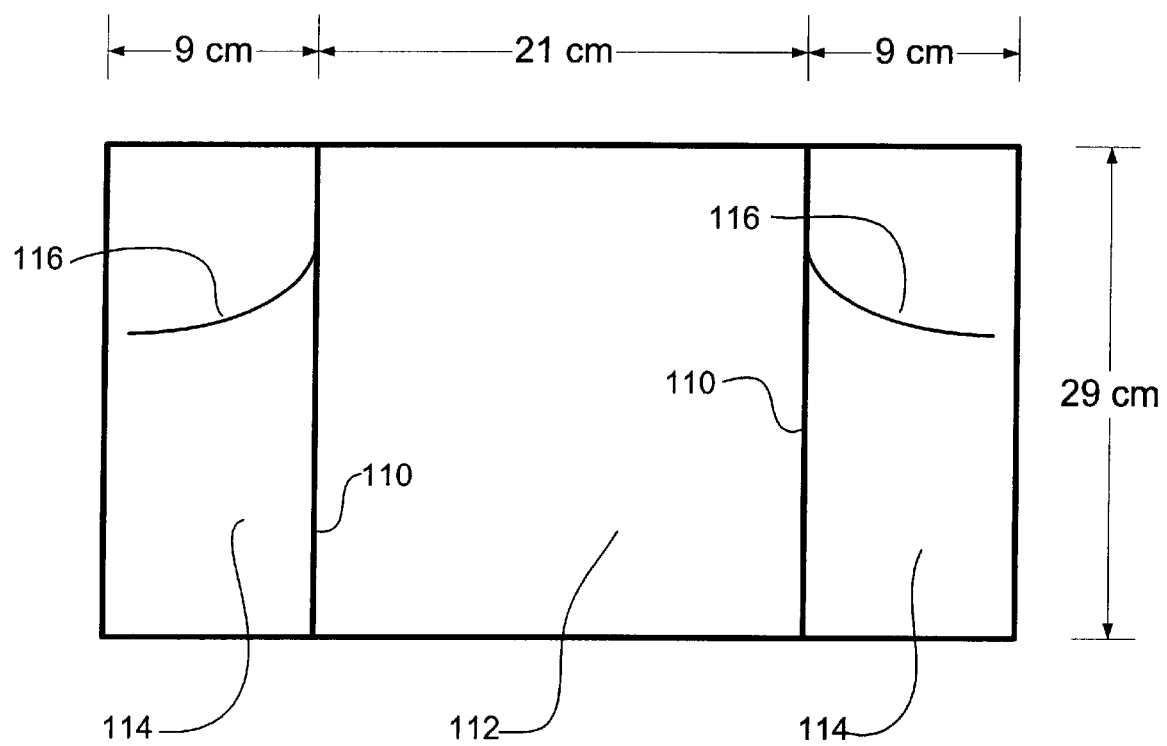
FIG. 5 is a schematic illustrating an intensity map field expanded by monotonically decreasing profile delivery.
Figure 6:
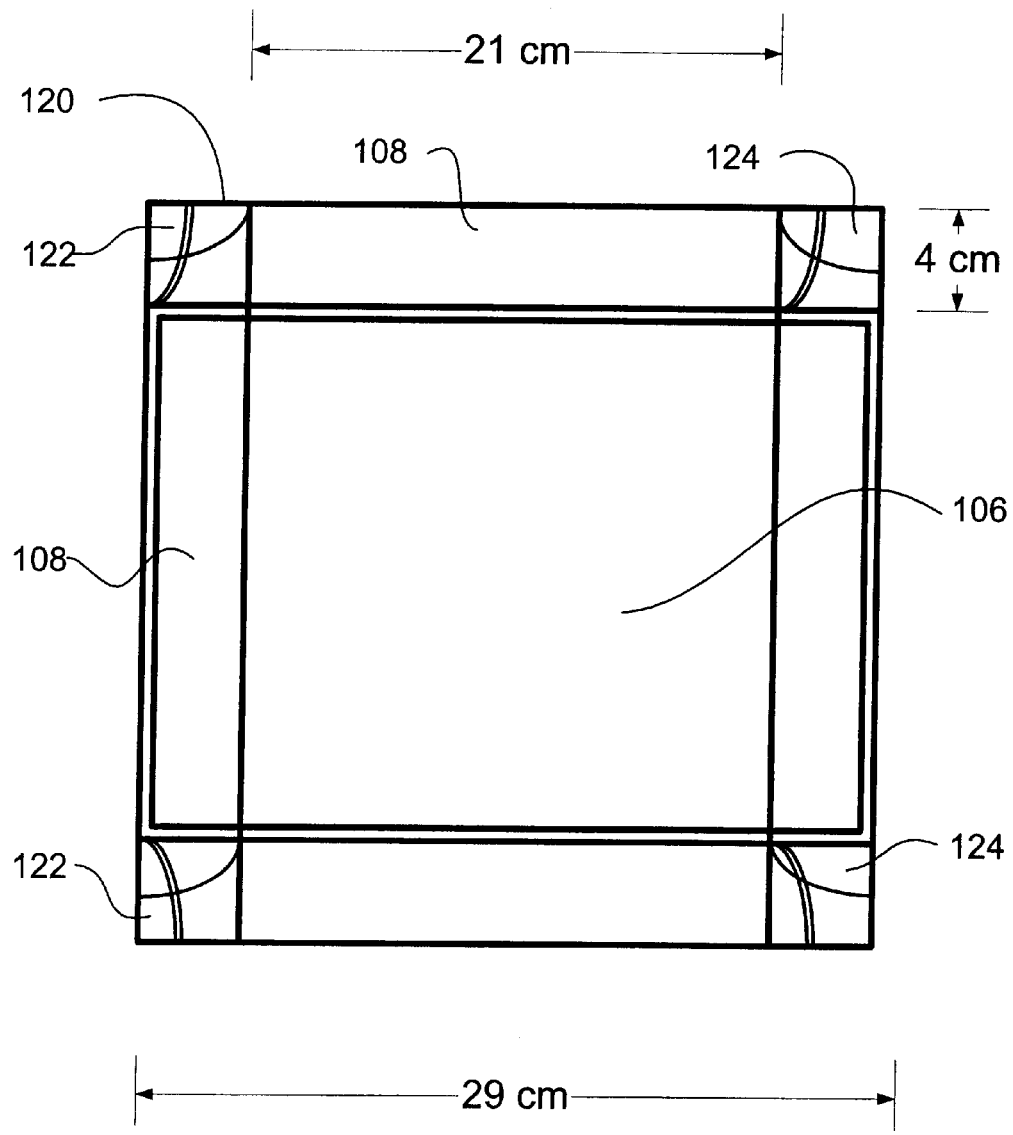
FIG. 6 is a schematic illustrating an intensity map field expanded using the orthogonal decomposition of FIG. 4 and the monotonically decreasing profile delivery of FIG. 5.
Figure 7:
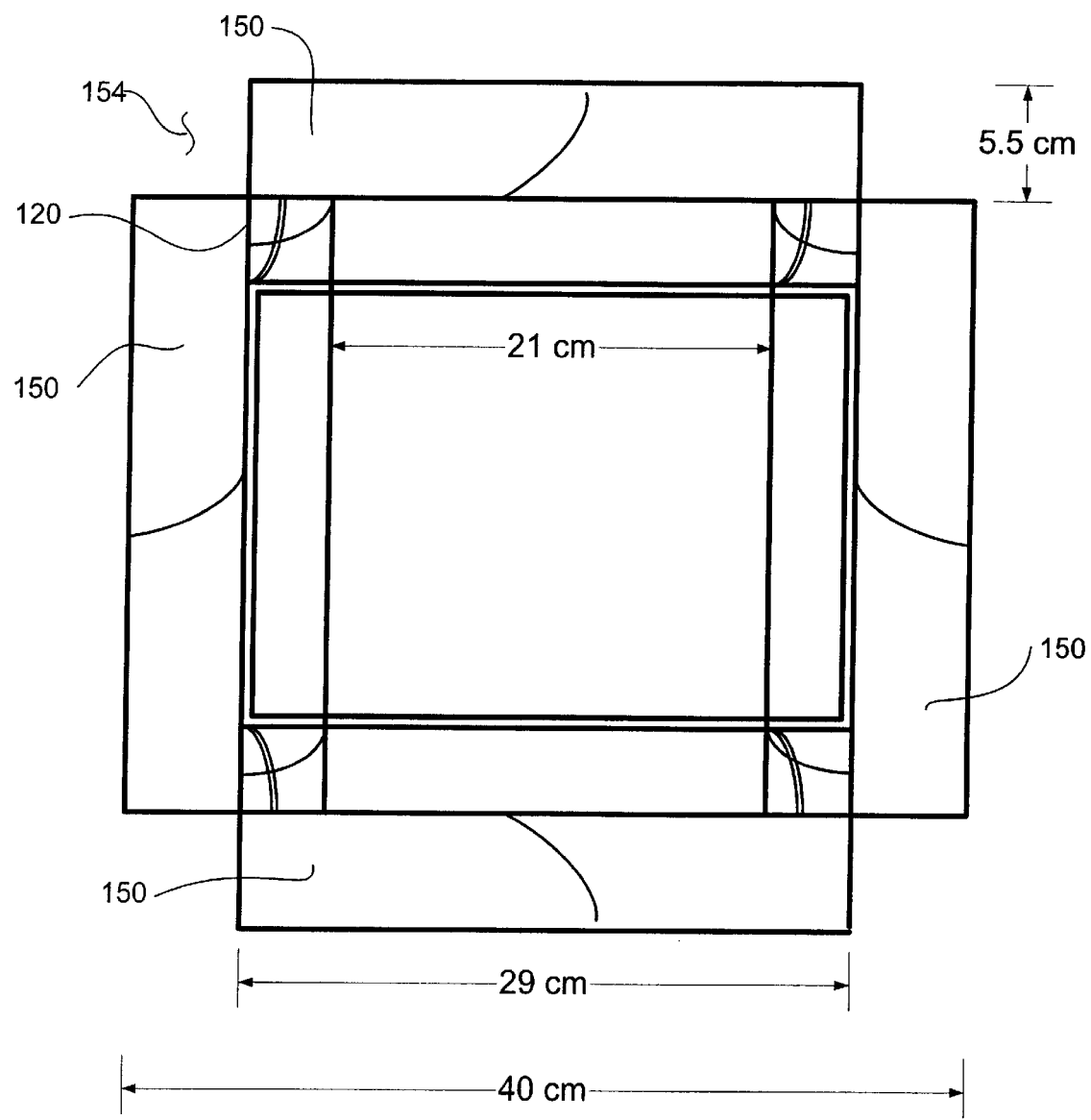
FIG. 7 is a schematic illustrating a field in which monotonically decreasing profiles are allowed for each leaf in both collimator settings.

As previously discussed, conventional treatment planning systems allow for only limited field sizes based on mechanical constraints of the multi-leaf collimator used to delivery a radiation treatment. The present invention allows these field size limitations for intensity maps to be relaxed providing the delivery of part of the intensity map in an orthogonal collimator setting. The over travel restrictions on the size of the intensity map in the leaf travel direction are further reduced by allowing for monotonically decreasing profiles in a direction away from the over travel edge. As described in detail below, orthogonal decomposition extends the field size to a central square with dimensions of the over travel*2 and four rectangles with dimensions equal to (number of leaves*leaf width/2) −central square dimension/2 and over travel*2 (FIG. 4). This field area does not have restrictions on the values of pencil beam intensities and arbitrary modulation patterns are allowed throughout the field. The field may further be expanded to a square with length and width equal to the number of leaves*leaf width, with the corner of the squares having horizontal and vertical component profiles that are monotonically decreasing away from the edge (FIGS. 5 and 6). Additional rectangles may also be added with the distributions in these rectangles having monotonically decreasing profiles away from the edge (FIG. 7). The dimensions of this field area are the largest possible field size (i.e., largest field opening for a leaf pair).

The following example details the three edge extension methods described briefly above for an intensity map field area. In this example, a multi-leaf collimator having 29 leaves and configured such that when outer jaws of the collimator move in to the first and outer set of leaves they all effectively have a width of 1 cm. The central leaf (leaf number 15) of the multi-leaf collimator passes through the isocenter and each leaf can over travel past the central axis by 10 cm. It is to be understood that this configuration is used only as an example and that other configurations of multi-leaf collimators having a different number or arrangement of leaves or a different leaf width may be used, without departing from the scope of the invention.

In this example, if an intensity map is positioned such that the isocenter falls inside of a pencil beam and the pencil beams are each 1 cm×1 cm in size, the intensity map can be delivered in either direction, since the leaves are 1 cm wide. In this case, the gridlines fall on half centimeter locations (e.g., 0.5, 1.5, 2.5. . . ) so that the most a leaf can move without exceeding the over travel limit of 10 cm is 9.5 cm. However, its partner in the leaf pair can move all the way out to 20 cm since it is not crossing the central axis and it has a range of 20 cm for normal travel. In the case where an arbitrary intensity map is required, the leaf pair can modulate the region between 9.5 cm and 10.5 cm. The map thus has 10.5 cm on either side of the central axis for a total range of 21 cm. This results in a maximum field size for an arbitrary map with the isocenter in the center of a 1 cm×1 cm pencil beam of 29 cm×21 cm (rectangle 102 in FIG. 4). However, since the central 21 cm×21 cm square can also be delivered with the multi-leaf collimator in its orthogonal collimator setting (i.e., collimator rotated 90 degrees from its zero offset position), an additional field with dimensions 21×29 (rectangle 104 defined by double lines in FIG. 4) can be superimposed on the first field 102. As shown in FIG. 4, this provides an expanded field area with a central 21 cm×21 cm square 106 and 4 cm×21 cm (or 21 cm×4 cm) edge margins (arms) 108 extending from the periphery of the central square along each side thereof. The entire field area (i.e., square 106 and arms 108) can have an arbitrary modulation pattern.

The intensity map may also have a monotonically decreasing profile extending away from over travel edges 110, as shown in FIG. 5. In this case only the leaf that is not beyond the central axis is moved so that no over travel is required. For example, if starting at 9.5 cm, the intensity profile has values 5, 5, 5, 4, 3, 2, 2, and 2, then only the right leaf has to move to generate this pattern and the left leaf can stay fixed at a position of 9.5 cm. This can also be done for a profile starting at −9.5 cm and going down towards −19.5 cm. In this case, the right leaf is fixed at −0.5 cm, while the left leaf is moved to generate the profile. Rather than being an arbitrary pattern as with the field areas 106 and 108 of FIG. 4, pattern 116 must be monotonically decreasing away from the over travel edge 110. (An example of a field which can be effectively treated using monotonic functions is shown in U.S. Pat. No. 5,724,403, which is incorporated by reference herein in its entirety.) This allows (without collimator rotation) a field size of 29 cm×39 cm, with the 29 cm×21 cm central area 112 having arbitrary patterns and the 29 cm×9 cm edge margins 114 having only patterns monotonically decreasing away from the central axis (FIG. 5). The upper limit for these decreasing profiles 116 are set by the left and right edge columns of the arbitrary 29 cm×21 cm intensity map.

Since in the above example collimator rotation is not being used, the pencil beams may use arbitrary column widths (e.g., 1 cm×5 mm) and they do not have to be centered on the isocenter. This provides an arbitrary 29 cm×21 cm matrix with edge extensions up to −20 and +20 (instead of −19.5 and 19.5) for a field size of 29 cm×40 cm. An arbitrary 29 cm×22 cm intensity map with extensions up to 40 cm can be provided with the use of a 1 cm×1 cm pencil beam with the isocenter located between two pencil beams.

The two concepts described above and shown in FIGS. 4 and 5 may be combined to generate a 29 cm×29 cm square 120 with inner square 106 and arms 108 having an arbitrary pattern and 4 cm×4 cm square corners 122, 124 made up of a superposition of monotonically decreasing profiles, as shown in FIG. 6. The double lines identify the fields for the orthogonal (90 degree offset) collimator setting and the single lines define the original (zero degree offset) collimator setting. Since each leaf can produce its own monotonically decreasing profile, more flexibility is provided in the types of two dimensional distribution due to the superposition of orthogonal profiles. For example, with the multi-leaf collimator geometry described above, the 4 cm×4 cm square corners may have the following matrices:

$$\begin{bmatrix} 2 & 3 & 3 & 4 \\ 1 & 3 & 4 & 4 \\ 0 & 1 & 2 & 2 \\ 2 & 3 & 4 & 5 \end{bmatrix} + \begin{bmatrix} 6 & 2 & 3 & 5 \\ 6 & 2 & 2 & 3 \\ 5 & 2 & 1 & 2 \\ 4 & 1 & 0 & 0 \end{bmatrix} = \begin{bmatrix} 8 & 5 & 6 & 9 \\ 7 & 5 & 6 & 7 \\ 5 & 3 & 3 & 4 \\ 6 & 4 & 4 & 5 \end{bmatrix}$$

While the first matrix has values in each row decreasing from left to right (left corners 122 of original collimator setting) and the second matrix has values in each column decreasing from top to bottom (bottom corners 124 of orthogonal collimator setting), the combined matrix (left bottom corner of the superposition of corners as viewed in FIG. 6) has profiles in its rows and columns that are not monotonic but have minima, in this example.

In addition to the 29 cm×29 cm square 120 of FIG. 6, monotonically decreasing profiles may be allowed for each leaf in both collimator settings. This provides 29 cm by 5.5 cm outer edge margins (arms) 150 extending from each side of the square 120 to cover a 40 cm×40 cm area, with 5.5 cm corners 154 removed (FIG. 7). If the same spacing between 1 cm×1 cm pencil beams is used, the arms 150 can only cover a 39 cm×39 cm area (see FIG. 5). However, the spacing for the arms 150 does not have to be the same as the spacing for the rest of the intensity map, since it is not involved in any superposition. The arms 150 may use, for example, 1 cm×0.5 cm to allow for 29 cm×5.5 cm arms 150 to cover the full 40 cm×40 cm area, which is the limit of motion for the leaves.

The only areas not covered in FIG. 7 are the 5.5 cm corner squares 154. However, since the primary collimator provides a radius of 25 cm and the beam would have clipped corners inside this area, these areas should not be included. In fact, in this shape, the farthest point from the isocenter is the corners of the arms 150 at $(14.5+20^2)^{0.5}=24.7$, which is just inside the primary collimator dimension.

Virtual micro intensity modulation radiation therapy, such as described in U.S. Pat. No. 6,134,296, may also be used in the 29 cm×29 cm square 120 to provide 0.5 cm×0.5 cm resolution. The virtual micro intensity modulation may be used, for example, in the central 21 cm×21 cm square 106, in the arms 108, and in the 4 cm×4 cm corners 122, 124 for the monotonically decreasing profiles. This provides a 29 cm×29 cm square with a resolution of 0.5 cm×0.5 cm and the arms 150 may also be included with a 1 cm×0.5 cm resolution (FIGS. 6 and 7).

A treatment planning system is generally configured to create arbitrary patterns. A filter is preferably provided to filter these arbitrary patterns and create patterns compatible with the edge extension techniques previously described. For example, a portion of the arbitrary patterns may be filtered to create monotonically decreasing profiles in regions 122, 124, and 150 of FIGS. 6 and 7.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for defining an extended field area of an intensity map for use in delivering radiation from a radiation source to an object with a multi-leaf collimator having a plurality of leaves operable to travel in a first direction and rotatable such that the leaves are operable to travel in a second direction extending generally orthogonal to said first direction, the method comprising:
    defining a central square area having dimensions approximately equal to two times an over travel margin of the multi-leaf collimator; and
    defining four edge margins each extending from a side of said central square and having dimensions approximately equal to two times an over travel margin of the multi-leaf collimator along an edge adjacent to said central square, and half the number of leaves within the multi-leaf collimator times leaf width minus half the dimension of the central square;
    wherein said central square and four edge margins define a field area for an intensity map deliverable with the multi-leaf collimator in two positions such that leaves travel in said first and second directions.

2. The method of claim 1 further comprising creating an intensity map for the defined field area.

3. The method of claim 2 further comprising delivering radiation with the multi-leaf collimator using the intensity map created for the defined field area.

4. The method of claim 1 further comprising creating an arbitrary modulation pattern for the field area.

5. The method of claim 1 wherein the multi-leaf collimator is configured such that each of the leaves can over travel past a central axis by at least 10 cm and the intensity map is positioned such that an isocenter is located inside of a 1 cm by 1 cm pencil beam, wherein said central square area is approximately 21 cm by 21 cm.

6. The method of claim 5 wherein the multi-leaf collimator comprises at least 29 leaves each having a leaf width of 1 cm, wherein said edge margins have dimensions of approximately 21 cm by 4 cm.

7. The method of claim 1 further comprising expanding the field area to include four corner squares each having two sides adjacent to two of said edge margins extending from adjacent sides of said central square.

8. The method of claim 7 further comprising creating a monotonically decreasing pattern for the expanded field area.

9. The method of claim 8 further comprising creating an arbitrary modulation pattern for said central square and said edge margins.

10. The method of claim 8 wherein the monotonically decreasing patterns decrease in a direction away from an over travel edge of the defined field area.

11. The method of claim 7 further comprising defining four outer edge margins each located adjacent to one side of a square defined by the original defined field area and the expanded field area.

12. The method of claim 11 further comprising creating a monotonically decreasing pattern within said outer edge margins.

13. The method of claim 1 further comprising increasing the resolution of the defined field area using virtual micro intensity modulation radiation treatment.

14. A system for defining an intensity map for use in delivering radiation from a radiation source to an object using a multi-leaf collimator having a plurality of leaves operable to travel in a first direction and rotatable such that the leaves are operable to travel in a second direction extending generally orthogonal to said first direction, the system comprising a processor operable to define a central square area having dimensions approximately equal to two times an over travel margin of the multi-leaf collimator, and define four edge margins each extending from a side of said central square and having dimensions approximately equal to two times an over travel margin of the multi-leaf collimator along an edge adjacent to said central square and half the number of leaves within the multi-leaf collimator times leaf width minus half the dimension of the central square, wherein said central square and four edge margins define a field area for an intensity map deliverable with the multi-leaf collimator in two positions such that leaves travel in said first and second directions; and memory configured to at least temporarily store an intensity map created for the defined field area.

15. The system of claim 14 wherein the processor is further configured to expand the field area to include four corner squares each having two sides adjacent to two of said edge margins extending from adjacent sides of said central square.

16. The system of claim 15 wherein said central square and said edge margins contain an arbitrary modulation pattern and said expanded field area contains a monotonically decreasing pattern.

17. A method for delivering radiation from a radiation source to an extended field area with a multi-leaf collimator having a plurality of leaves operable to travel in a first direction and rotatable such that the leaves are operable to travel in a second direction extending generally orthogonal to said first direction, the method comprising creating an intensity map having boundaries defined by two rectangles each having dimensions approximately equal to two times an over travel margin of the multi-leaf collimator and the number of leaves of the multi-leaf collimator times leaf width, the two rectangles arranged such that the center of the rectangles have the same central axis and are positioned orthogonal to one another.

18. The method of claim 17 further comprising delivering radiation with the collimator in a zero degree offset position with the leaves moving in said first direction and delivering radiation with the collimator in a ninety degree offset position with the leaves moving in said second direction.

19. The method of claim 17 wherein the boundary of the intensity map further includes four corner squares located at a periphery of the two rectangles such that the intensity map boundary is generally square.

20. The method of claim 19 wherein creating an intensity map comprises creating an arbitrary modulation pattern within the two rectangles and a monotonically decreasing pattern within the four corner squares.

* * * * *